United States Patent
Robert et al.

(10) Patent No.: US 6,872,749 B2
(45) Date of Patent: Mar. 29, 2005

(54) METHOD FOR SUPPLYING BIOAVAILABLE METHIONINE TO A COW

(75) Inventors: Jean-Claude Robert, Neris les Bains (FR); Robert Bennett, Gif sur Yvette (FR); Georges Gros, Antony (FR)

(73) Assignee: Adisseo Ireland Limited (IE)

( * ) Notice: Subject to any disclaimer, the term of this patent is extended or adjusted under 35 U.S.C. 154(b) by 173 days.

(21) Appl. No.: 10/336,912

(22) Filed: Jan. 6, 2003

(65) Prior Publication Data

US 2003/0143260 A1 Jul. 31, 2003

Related U.S. Application Data

(63) Continuation of application No. 10/060,327, filed on Feb. 1, 2002, now Pat. No. 6,528,541.

(30) Foreign Application Priority Data

Nov. 13, 1998 (FR) .............................. 98 14249
Jul. 29, 1999 (FR) .............................. 99 10050

(51) Int. Cl.$^7$ .............................. A61K 31/22
(52) U.S. Cl. .................................... 514/550
(58) Field of Search .......................... 514/550

(56) References Cited

U.S. PATENT DOCUMENTS

| 3,952,115 | A | * | 4/1976 | Damico et al. | ............. | 426/590 |
| 5,084,482 | A | * | 1/1992 | Hirsch et al. | ............. | 514/562 |
| 5,871,773 | A | * | 2/1999 | Rode et al. | ............. | 424/438 |
| 5,885,610 | A | * | 3/1999 | Anderson | ............. | 424/438 |
| 6,017,563 | A | * | 1/2000 | Knight et al. | ............. | 426/2 |
| 6,221,909 | B1 | | 4/2001 | Robert et al. | | |

FOREIGN PATENT DOCUMENTS

| AU | 478 542 | | 9/1975 | | |
| AU | 478542 | * | 9/1975 | ............. | 514/550 |
| FR | 2 305 938 | | 10/1976 | | |
| WO | WO 99/04647 | | 2/1999 | | |

OTHER PUBLICATIONS

Ayoade et al, J. Sci. Food Agric., vol. 33, pp. 949–956 (1982).*

Patterson et al., "Metabolism of DL–Methionine and Methionine Analogs by Rumen Microorganisms", J. Dairy Sci. 71:3292–3301 (1988).

Ayoade et al., "Studies of Methionine Derivatives as Possible Sources of Protected Methionine in Ruminant Rations", J. Sci. Food Agric. 33:949–956 (1982).

Schwab, "Methionine Analogs for Dairy Cows: A Subject Revisited", pp. 1–25, Prepared for 1998 California Animal Nutrition Conference, Fresno, CA.

Fotouhi et al., "Resistance of Fatty Acyl Amides to Degradation and Hydrogenation by Ruminal Microorganisms", J. Dairy Sci. vol. 75, pp. 1527–1532 (1992).

Co–pending application No. 10/060, 327, filed on Feb. 1, 2002.

* cited by examiner

*Primary Examiner*—James H Reamer
(74) *Attorney, Agent, or Firm*—Connolly Bove Lodge & Hutz LLP

(57) ABSTRACT

The present invention relates to a method for supplying bioavailable methionine to a cow which comprises supplying to the cow an ester of methionine or methionine amide and/or an ester of the hydroxy analogue of methionine or a salt thereof.

9 Claims, No Drawings

METHOD FOR SUPPLYING BIOAVAILABLE METHIONINE TO A COW

This application is a continuation of application Ser. No. 10/060,327, filed Feb. 1, 2002, now U.S. Pat. No. 6,528,541, which is a continuation of application Ser. No. 09/794,347 filed Feb. 28, 2001, now U.S. Pat. No. 6,372,788, which is a continuation of application Ser. No. 09/438,521 filed Nov. 12, 1999, now U.S. Pat. No. 6,221,909.

This application claims the benefit of foreign priority to French patent application no. 98 14249, filed Nov. 13, 1998, and French patent application no. 99 10050, filed Jul. 29, 1999. Both of these foreign priority documents are incorporated by reference herein.

The present invention relates to a method for supplying bioavailable methionine to a cow which comprises administering to the cow an ester of methionine or methionine amide and/or an ester of the hydroxy analogue of methionine or a salt thereof. The present invention also relates to a method of improving milk obtained from dairy cows and in particular to a method which comprises supplying to the dairy cow an ester of methionine or methionine amide and/or an ester of the hydroxy analogue of methionine or a salt thereof.

Protein is one of the major nutrients in the diets of lactating cows. The cows however do not actually require proteins but instead they require the specific amino acids, which are the building blocks that make up their own protein.

It is known that methionine is a limiting amino acid and in particular for milk production it is believed that a well balanced level of methionine will result in effective levels of milk production. It is also believed that an increase in methionine levels can result in increased milk production.

It is therefore desirable to maintain or even enhance the level of methionine. Methionine can be added directly to the cow's diet. However, the free form of this amino acid is rapidly degraded by bacteria in the rumen and consequently only a small portion of the methionine enters the bloodstream. There have been many attempts to overcome this problem and in general the methionine is introduced into the diet in a protected or modified form, permitting the compound to pass through the rumen unaffected. The methionine released from the protected or modified form then enters the small intestine and is absorbed into the bloodstream. One of the most widely studied compounds for this particular purpose is the hydroxy analogue of methionine, namely 2-hydroxy-4-(methylthio) butanoic acid, generally referred to as HMB.

WO 99/04647, published on Feb. 4, 1999, discloses a method of introducing methionine into the rumen by supplementing the feed with the hydroxy analogue of methionine. In this patent application, it is claimed that the hydroxy analogue is substantially unaffected by rumen degradation, passing through the rumen and consequently providing at least 20%, preferably at least 40% of the hydroxy analogue for absorption into the bloodstream through the intestine. The patent application refers to the hydroxy analogue, its salts, esters, amides and oligomers as being 'rumen by-pass' and claims an improved efficient means of introducing methionine into the bloodstream of the cow. The claimed advantage of the disclosed compounds in this documents is that the compounds by-pass the rumen and are absorbed in the intestine.

There are also many publications on the effect of the hydroxy analogue of methionine and a publication by Charles Schwab, from a presentation given at a conference in May 1998, reviews all of the publications and concludes that the hydroxy analogue of methionine is thought to by-pass the rumen for intestinal absorption but will only do so if it is administered at a dose above 60 g per animal per day, preferably above 90 g per animal per day. At lower doses, it would appear, according to the author, that the hydroxy analogue of methionine is to a large extent, consumed by the micro organism in the rumen.

The best determination of the absorption of the hydroxy analogue of methionine is the determination of the bioavailability in the blood. The bioavailability is characterised by the level of appearance of methionine in the blood compared with the amount of methionine equivalent of compound introduced into the feed ration. This determination takes into account the passage of the hydroxy analogue through the rumen, its degree of absorption irrespective of the place of absorption during the digestive transit and the degree enzymatic conversion of the hydroxy analogue into methionine. At a dose of methionine equivalent to 50 g per day per cow, it is described in this article that methionine protected against degradation in the rumen with a polymer, in particular the product sold under the trade name Smartamine™, has a rumen by-pass of 90%; the hydroxy analogue gives a bioavailability of only 3%.

A paper in J Dairy Science 1988, 71, pp 3292 to 3301 discloses the introduction of the methyl ester or the ethyl ester of the hydroxy analogue of methionine to the diet of a cow in an attempt to increase the level of milk production. The results from the study indicate that these esters are rapidly converted to the hydroxy analogue of methionine and subsequently degraded in the rumen of the animal. Specifically, after incubation for six hours in rumen juices, only 1.8% and 3% of the methyl and ethyl ester of the hydroxy analogue respectively, remains. This is compared with 34% and 85% of methionine and the hydroxy analogue of methionine.

We have now found, contrary to the teachings of the aforementioned prior art, that certain esters of methionine or a methionine amide and/or the hydroxy analogue of methionine have a favourable effect in cows. We have surprisingly found that certain compounds introduce methionine into the bloodstream of the rumen more effectively and more rapidly than the known prior art. We have also found that these particular compounds do not enter the bloodstream through rumen by-pass and intestinal absorption but by absorption through the rumen wall. We have also found that introducing the specific ester compound into the diet of dairy cows through the feed ration results in desired improvement in milk production.

Accordingly the present invention provides a method for supplying bioavailable methionine to a cow which comprises administering to the cow an ester of methionine or methionine amide and/or an ester of the hydroxy analogue of methionine or a salt thereof.

For the purposes of the present invention, by cow is meant cattle, namely beef cows and dairy cows.

In particular the present invention provides a method for supplying bioavailable methionine to a cow which comprises administering to the cow a branched alkyl ester of methionine or methionine amide and/or a branched alkyl ester of the hydroxy analogue of methionine.

The use of the claimed esters provides the advantage over the prior art in that it provides a greater amount of methionine into the bloodstream of the cow than the methionine derivatives of the prior art. Furthermore, we have surprisingly found that the use of the particular esters results in very rapid absorption of methionine into the bloodstream. The ester derivatives according to the present invention appear not only to avoid rumen degradation but surprisingly introduce methionine into bloodstream by absorption through the rumen wall. This is contrary to the aforementioned prior art wherein the hydroxy analogue compounds of methionine are known to either degrade in the rumen or by-pass the rumen and absorb through the intestine.

As is evident from the prior art in this area, studies to introduce methionine into the bloodstream of the ruminant have concentrated on the use of rumen by-pass compounds as the quickest and most effective means of introducing methionine into the bloodstream. We have found that the addition of the esters of the present invention to the diet of the cow can result, in some cases, in more than 50% of methionine equivalent being absorbed directly through the rumen wall. Not only do these esters have a high bioavailability level but they allow methionine or biologically equivalent compounds to enter the blood steam very quickly after intake by the cow through rumen absorption. This result is surprising and quite unexpected because until now, it has actually been believed that only compound such as volatile fatty acids, ammonia and dioxycarbons are absorbed through the rumen wall.

The present invention also seeks to provide an improvement in the condition of the cow and the use of the specific esters of the present invention can result in an improvement in the weight gain, an improvement in the fertility, an increase in energy as well as an improvement in the function of the liver.

The effect on the liver function as a result of the administration of the ester is an important benefit. This effect may be characterised by a reduction in metabolic problems through an improvement in the very low density lipoproteins. Also thought likely, is a reduction in blood ketosis and a limitation of hepatic steatosis.

The administration of the ester can also have a beneficial effect on reproduction. The interval between calving and reproduction may be shortened. This effect is also characterised by an increase in the percentage fertilisation during insemination.

It also appears that the use of the specific esters may result in a stimulation of rumen fermentation, thus resulting in more digestible organic matter and therefore more energy.

We have also found that when the esters of the present invention are given to dairy cows, there is an improvement in the milk obtained thereof.

According to another aspect of the present invention, there is provided a method of improving milk from a dairy cow which comprises administering to the cow an ester of methionine or methionine amide and/or an ester of the hydroxy analogue of methionine or a salt thereof.

In particular, the present invention provides a method of improving milk from a dairy cow which comprises administering to the cow a branched alkyl ester of methionine or a branched alkyl ester of the hydroxy analogue of methionine.

Where the esters of the present invention are supplied to dairy cows we have found that by supplementing the normal daily feed of the dairy cow with an ester of methionine or methionine amide and/or an ester of the hydroxy analogue of methionine or a salt thereof, there is a surprising improvement in the quality of the milk obtained from the dairy cow. In particular, we have found that the introduction of the specific esters into the diet of the dairy cow results in an increase in the protein content of the milk.

Furthermore, in addition to the protein level, it has been found that the administration of the specific esters of methionine or methionine amide and/or esters of the hydroxy analogue of methionine or a salt thereof can result in improvements in the volume of milk produced and the fat content of the milk.

The increase in protein content as a result of the administration of the ester can be evaluated as being generally between 0.5 and 4 g of protein per liter of milk. The proteins which are generally increased are alpha, beta and kappa, especially the beta and kappa proteins which have a favourable effect on the cheese making properties of the milk produced.

The foregoing objects may be obtained in whole or in part.

The present invention is directed to a method of supplying bioavailable methionine to the cow which comprises administering to the cow an ester of methionine or methionine amide and/or ester of the hydroxy analogue of methionine or a salt thereof. Suitable esters are alkyl esters. The alkyl group may be linear, branched or cyclic having 1 to 12 carbon atoms, preferably 1 to 10, most preferably 1 to 4 carbon atoms.

Suitable esters of methionine and the hydroxy analogue of methionine include the methyl ester, ethyl ester, n-propyl ester, isopropyl ester, butyl esters, namely n-butyl ester, sec butyl ester, isobutyl ester and tertiary butyl ester, pentyl esters and hexyl esters, especially n-pentyl, isopentyl, n-hexyl and isohexyl esters. Suitable amides of methionine included the alkyl ester of N-acyl methioninates for example alkyl N-acetyl methioninates.

Preferably, the ester is a branched or linear alkyl ester, especially a branched alkyl ester, for example the isopropyl ester and the tertiary butyl ester. As regards the ester of methionine, the most preferred is the isopropyl ester and tertiary butyl ester. As regards the hydroxy analogue of methionine, the most preferred is the tertiary butyl and the isopropyl ester.

In particular, it has been found that the use of the isopropyl ester of the hydroxy analogue of methionine is particularly effective, being capable of providing at least 50% of methionine equivalent to the bloodstream by absorption across the rumen wall. The isopropyl ester of the hydroxy analogue of methionine has been found to display a bioavailability of methionine of more than 50%.

Furthermore it has been found that with the isopropyl ester of the hydroxy analogue, the bioavailability peak appears, in the blood relatively quickly following the administration indicating, that the ester is absorbed directly through the rumen wall thus indicating that the ester is not rumen by-pass.

It has also been found that the tertiary butyl ester of methionine is capable of providing approximately 80% methionine equivalent to the cow by rumen absorption. This specific ester also appears to enter the blood stream very quickly, providing methionine within less than one hour of intake.

The ester may be supplied to the cow in any suitable way. Preferably, the ester is supplied as a feed supplement and may be supplied to the cow through the normal daily feed. Cows are fed a ration which comprises a concentrate portion and a forage portion. According to another aspect of the present invention there is provided a ration comprising a forage portion, a concentrate portion and a supplement, said supplement comprising an ester of methionine or methionine amide and/or an ester of the hydroxy analogue of methionine or a salt thereof.

Suitable esters in the ration are esters as hereinbefore described. A preferred ration comprises a forage portion, a concentrate portion and the isopropyl ester of the hydroxy analogue of methionine.

The amount of ester introduced into the feed of the cow may vary from the breed of cow and from the stage of the milk producing cycle. Suitably, the supplement comprises an amount of ester calculated as methionine equivalent of up to 75 g, preferably from 5 to 50 g, especially from 10 to 30 g per animal per day.

The amount of ester required may be calculated using any suitable means familiar to the person skilled in the art. Suitably, the amount may be determined through the use of a computer model.

Where the ration contains the tertiary butyl ester or the isopropyl ester of the hydroxy analogue of methionine, the ester may be present in a concentration of from 7 to 65 g per animal per day, most preferably from 10 to 30 g per animal per day of ester. Where the ration contains the isopropyl ester or the tertiary butyl ester of methionine, the ration suitably comprises from 7 to 65 g, most preferably from 10 to 30 g of the ester.

According to another aspect of the present invention there is provided a unit dosage form comprising an amount of ester as herein before described suitable for dosage for one cow for one day.

The forage portion may typically comprise corn silage, grass silage, alfalfa silage and/or hay silage. The concentrate portion may typically comprise grains such as corn, wheat, barley in addition to sources of protein such as meal, rape seed, soyabean, corn gluten and by products such as fish meal, blood meal, brewers grain and the like.

The supplement comprising the ester may be mixed with the forage portion and the grain portion at any suitable time. The ester is a liquid and may be introduced by mixing in with the forage portion and the concentrate portion prior to the formation of the food pellets. Alternatively, the ester may be added to the pellet ration by the farmer prior to feeding to the cow.

The ester when incorporated into the feed pellet either before or after formation of the pellet is stable. In particular, it has been found that the isopropyl ester of the hydroxy analogue is stable in the resulting pellet, retaining over 95% stability over a long period. Thus, the use of the esters of the present invention as a food supplement provides a stable source of methionine.

The present invention will now be described in detail with reference to the following examples wherein

EXAMPLE 1

Esters of the Hydroxy Analogue of Methionine (a) Preparation of the Esters:

(1) Isopropyl Ester of the Hydroxy Analogue of Methionine 314.4 g (1.88 mol) of 2 hydroxy-4 methylthiobutyronitrile was placed in a stirred jacket reactor fitted with chicanes. 201.3 g (1.951 mol) of 95% sulphuric acid was added slowly whilst maintaining the temperature below 50° C. After the introduction of the acid, the reaction temperature was maintained at 45° C. for 15 minutes. 227.3 g of isopropanol was added to the reactor contents. The temperature of the reactor was then increased at a rate of 5° C. per minute until the temperature at the bottom of the reactor reached 116° C. and the temperature at the top reached 75° C. These reactor conditions were maintained for 5 hours. Some of the distillate was removed during that period and replaced with fresh isopropanol.

The reaction mixture was then neutralized with 161.2 g of 32% aqueous ammonia (2.72 mol of ammonia). Two phases were obtained. 780 g of water and 449.7 g of dichloromethane were added. The two resulting phases were separated to yield 939.1 g of organic phase and 1247.4 g of aqueous phase.

The light fractions of the organic product were removed by distillation. The temperature of the evaporating bath was increased and the pressure reduced to approximately a few milibars. 263.5 g of distillate was recovered. The titre of isopropyl ester of methionine was found to be greater that 99%. The yield was 72%.

(2) Methyl, Ethyl, -Butyl and Cyclohexyl Esters of the Hydroy Analogue of Methionine These esters were prepared as detailed above but using the appropriate alcohol.

(b) Bioavailability

Spot doses of the following amounts of the esters prepared as detailed above, equating to 50 g of methionine equivalent, were given to 2 cows in the manner described in Example 2(b1) above.

methyl ester of HMB: 64.8 g ethyl ester of HMB: 74.8 g isopropyl ester of HMB: 80.5 g n-butyl ester of HMB: 96 g cyclohexyl ester of HMB: 97.5 g see butyl ester of HMB: 79 g The concentration of methionine and HMB was measured over a period of 27 hours. The measurements were plotted and the areas under the curve calculated to provide the bioavailability results.

Bioavailability was determined with reference to Smartamine™.

The bioavailability results of the esters are given in Table 1

TABLE 1

BIOAVAILABILITY RESULTS
ESTERS OF THE HYDROXY ANALOGUE OF METHIONINE (HMB)

| Ester | Time after administration (hours) | 0 | 1 | 2 | 3 | 5 | 7 | 27 | Bioavailability |
|---|---|---|---|---|---|---|---|---|---|
| Isopropyl | [met]* | 0.27 | 1.53 | 1.96 | 2.49 | 2.93 | 2.93 | 1.00 | 59% |
| ester of HMB | [HMB]* | 0 | 1.90 | 1.00 | 0.99 | 0.38 | 0.30 | 0 | |
| Methyl ester | [met]* | 0.42 | 1.26 | 1.58 | 1.64 | 1.66 | 1.86 | 0.53 | 39% |
| of HMB | [HMB]* | 0 | 1.35 | 0.60 | 0.65 | 0.30 | 0.33 | 0 | |
| ethyl ester of | [met]* | 0.44 | 1.61 | 1.87 | 1.94 | 1.97 | 2.13 | 0.66 | 35% |
| HMB | [HMB]* | 0.00 | 2.39 | 0.92 | 0.50 | 0.27 | 0.32 | 0 | |
| n-butyl ester | [met]* | 0.33 | 0.67 | 0.70 | 0.74 | 0.91 | 1.07 | 0.49 | 17% |
| of HMB | [HMB]* | 0.00 | 0.23 | 0.12 | 0.15 | 0.26 | 0 | 0 | |
| Sec butyl | [met]* | 0.31 | 1.25 | 1.48 | 1.53 | 1.14 | 1.22 | 0.42 | 31% |
| ester of HMB | [HMB]* | 0 | 2.15 | 1.06 | 0.59 | 0.42 | 0.52 | 0 | |
| cyclohexyl | [met]* | 0.36 | 0.55 | 0.87 | 1.06 | 1.07 | 1.09 | 0.47 | 20% |
| ester of HMB | [HMB]* | 0.00 | 0.36 | 0.21 | 0.23 | 0.26 | 0.24 | 0 | |

*concentration measured in mg/100 g of blood plasma;
met = methionine

EXAMPLE 2

Esters of Methionine (a) Preparation of Esters

The esters of methionine were prepared according to the following general procedure:

Methionine and 1.2 eq of sulphuric acid relative to the methionine to be esterified were introduced into the alcohol corresponding to the nature of the alkyl chain. The resulting mixture was refluxed whilst removing water to shift the equilibrium. The mixture was neutralised with ammonia to isolate the ester. The alcohol was distilled off. The ester obtained was extracted with dichloromethane and washed with water. The dichloromethane was evaporated.

The esters of methionine prepared according to this process are: methyl methioninate, -propyl methioninate, -butyl methioninate, n-hexyl methioninate, -octadecyl methioninate, ethyl N-acetyl methioninate, methionine methyl ester hydrochloride, methionine ethyl ester hydrochloride, isopropyl methioninate, tertiary butyl methioninate, cyclohexyl methioninate, sec butyl methioninate and dodecyl methioninate.

(b) Bioavailability

The bioavailability of the esters was evaluated.

(1) Methyl Methioninate and n-propyl Methioninate 56 g of methyl methioninate and 72 g of n-propyl methioninate (providing an equivalent 50 g of DL-methionine), prepared as detailed above, were supplied to two cows as a spot dose at 7.45 am just before the morning feed.

The ration given to the cows was distributed as two equal meals at 08.00 hours and 16.00 hours comprised 7 kg of hay and 2 kg concentrate.

| WEEK | COW 1 | COW 2 |
|---|---|---|
| 1 | methyl methioninate | -propyl methioninate |
| 2 | — | — |
| 3 | n-propyl methioninate | methyl methioninate |
| 4 | — | — |

Samples of blood were taken by jugular vein puncture 09.00, 10.00, 11.00, 13.00 and 15.00 hours on the day where the ester was given to the animal and at 09.00, 12.00 and 15.00 hours on the day before and two days after supply.

The plasma from each sample was isolated from the blood samples by centrifuging the blood at 3000 revs per minute for 10 minutes. The samples were stored in a freezer. The assay for methionine was carried out according to the standard procedure of Moore and Stein.

The results were plotted using the conventional AUC method wherein the areas under the curves are calculated to obtain the bioavailability values for each ester.

The bioavailability results for the esters are given in Table 2

(2) n-hexy Methioninate, -butyl Methioninate, n-octadecyl Methioninate, ethyl N-acetyl Methioninate Spot doses of the following amounts of the esters prepared as detailed above, equating to 50 g of methionine, were given to 2 cows in the manner described in (b1) above.

n-hexy methioninate: 79 g n-butyl methioninate: 86 g n-octadecyl methioninate: 227 g ethyl N-acetyl methioninate: 75 g The ration given to the cows was distributed as two equal meals at 08.00 hours and 16.00 hours and comprised 7 kg of hay and 2 kg concentrate comprising 41% barley, 37% dehydrated beet pulp, 5% molasses, 2% urea and 15% soyabean 48.

The esters were given to the cow according to the following schedule:

| WEEK | COW 1 | COW 2 |
|---|---|---|
| 3 | butyl methioninate | octadecyl methioninate |
| 5 | octadecyl methioninate | n-hexyl methioninate |
| 7 | ethyl N-acetyl methioninate | n-butyl methioninate |
| 10 | n-hexyl methioninate | ethyl N-acetyl methioninate |

The bioavailability results for the esters are given in Table 2.

(3) Methionine Ethyl Ester Hydrochloride

The procedure of (b1) was repeated using 72 g of methionine ethyl ester hydrochloride, prepared as detailed above The daily ration given to the cows was as in (b2).

The ester was given to the cow according to the following schedule:

| WEEK | COW 1 | COW 2 |
|---|---|---|
| 1 | methionine ethyl ester hydrochloride | methionine ethyl ester hydrochloride |
| 2 | — | — |

Blood samples were taken at the same times as in (b1)

The bioavailability result for this ester is given in Table 2.

(4) Dodecyl Methioninate and Isopropyl Methioninate 106.5 g of dodecyl methioninate and 64.1 isopropyl methioninate (providing an equivalent 50 g of DL-methionine), prepared as detailed above, were supplied to two cows as detailed in (b1) above.

The esters were given to the cow according to the following schedule:

| WEEK | COW 1 | COW 2 |
|---|---|---|
| 3 | isopropyl methioninate | isopropyl methioninate |
| 5 | isopropyl methioninate | isopropyl methioninate |
| 7 | dodecyl methioninate | dodecyl methioninate |

Blood samples were taken from each cow according to the regime of (b1).

The bioavailability results for the esters are given in Table 2

(5) Cyclohexyl Methioninate, Methionine Methyl Ester Hydrochloride and Sec Butyl Methioninate Spot doses of the following esters prepared as detailed above, equating to 50 g equivalent of methionine were given to 2 cows in the manner described in (b1) above:

cyclohexyl methioninate: 122 g methionine methyl ester hydrochloride: 73 g sec butyl methioninate: 72 g The bioavailability results are given in Table 2

TABLE 2

BIOAVAILABILITY RESULTS
ESTERS OF METHIONINE

| ESTER | Time after administration (hours) | 0 | 1 | 2 | 3 | 5 | 7 | 28 | Bioavailability % |
|---|---|---|---|---|---|---|---|---|---|
| n-octadecyl methioninate | [met]* | 0.37 | 0.37 | 0.37 | 0.34 | 0.37 | 0.31 | 0.38 | 1 |
| Dodecyl methioninate | [met]* | 0.33 | 0.38 | 0.37 | 0.37 | 0.44 | 0.45 | 0.28 | 3 |
| n-butyl methioninate | [met]* | 0.32 | 1.10 | 0.74 | 0.63 | 0.62 | 0.61 | 0.27 | 8 |
| n-hexyl methioninate | [met]* | 0.31 | 1.22 | 0.92 | 0.94 | 1.06 | 1.07 | 0.35 | 17 |
| n-propyl methioninate | [met]* | 0.32 | 2.29 | 1.70 | 1.55 | 1.27 | 1.14 | 0.32 | 22 |
| ethyl N-acetyl methioninate | [met]* | 0.26 | 1.84 | 1.97 | 1.53 | 1.12 | 0.86 | 0.36 | 20 |
| Methionine ethyl ester hydrochloride | [met]* | 0.36 | 2.78 | 2.60 | 2.30 | 2.00 | 1.43 | 0.38 | 30 |
| Methyl methioninate | [met]* | 0.34 | 4.08 | 3.87 | 3.25 | 2.57 | 2.51 | 0.41 | 51 |
| Isopropyl methioninate | [met]* | 0.33 | 3.62 | 3.21 | 2.86 | 2.22 | 1.93 | 0.35 | 44 |
| Tertiary butyl methioninate | [met]* | 0.37 | 4.84 | 4.87 | 4.98 | 4.39 | 4.19 | 0.76 | 80 |
| Cyclohexyl methioninate | [met]* | 0.29 | 2.55 | 2.27 | 1.88 | 1.61 | 1.55 | 0.38 | 35 |
| Methionine methyl ester hydrochloride | [met]* | 0.41 | 1.96 | 1.43 | 1.27 | 1.18 | 1.22 | 0.43 | 25 |
| sec butyl methioninate | [met]* | 0.35 | 2.75 | 2.49 | 2.39 | 1.75 | 1.56 | 0.44 | 28 |

*concentration measured in mg/100 g of blood plasma;
met = methionine

EXAMPLE 3

Kinetics

The kinetics of availability of methionine and HMB in the bloodstream were determined for the isopropyl ester of the hydroxy analogue of methionine and compared with the hydroxy analogue of methionine (a compound not according to the present invention).

The procedure of Example 2 was repeated wherein samples of the isopropyl ester of the hydroxy analogue (69 g) and the hydroxy analogue (Alimet™-57 g) were given to four cows. The methionine and HMB levels in the blood plasma taken from the cows were analysed and the results are given in Tables 3 and 4 below.

It can be seen from the results that the isopropyl ester of the hydroxy analogue of methionine provides methionine and HMB to the bloodstream much quicker than HMB itself, thus indicating the ester is absorbed through the rumen wall.

TABLE 3

BLOOD PLASMA METHIONINE CONCENTRATIONS (mg/100 g of plasma)

| COMPOUND | Time after administration | 0 | 10 mins | 20 mins | 30 mins | 40 mins | 50 mins | 60 mins | 75 mins | 90 mins | 120 mins | 240 mins |
|---|---|---|---|---|---|---|---|---|---|---|---|---|
| HMB | COW 1 | 0.32 | 0.31 | 0.34 | 0.29 | 0.27 | 0.27 | 0.28 | 0.29 | 0.30 | 0.26 | 0.48 |
| HMB | COW 2 | 0.39 | 0.32 | 0.35 | 0.35 | 0.34 | 0.34 | 0.35 | 0.29 | 0.31 | 0.39 | 0.67 |
| HMB | COW 3 | 0.40 | 0.35 | 0.36 | 0.36 | 0.34 | 0.34 | 0.34 | 0.31 | 0.33 | 0.42 | 0.59 |
| HMB | COW 4 | 0.30 | 0.33 | 0.34 | 0.36 | 0.31 | 0.26 | 0.24 | 0.25 | 0.28 | 0.32 | 0.46 |
| Isopropyl ester of HMB | COW 1 | 0.33 | 0.72 | 1.00 | 1.13 | 1.30 | 1.46 | 1.60 | 1.69 | 1.74 | 1.96 | 2.12 |
| Isopropyl ester of HMB | COW 2 | 0.33 | 0.45 | 0.67 | 0.71 | 0.75 | 0.77 | 0.86 | 1.11 | 1.43 | 1.75 | 1.98 |
| Isopropyl ester of HMB | COW 3 | 0.37 | 0.37 | 0.50 | 0.76 | 0.89 | 1.05 | 1.10 | 1.21 | 1.44 | 1.68 | 2.39 |
| Isopropyl ester of HMB | COW 4 | 0.37 | 0.26 | 0.45 | 0.70 | 0.82 | 0.92 | 1.19 | 1.40 | 1.54 | 1.79 | 2.00 |

TABLE 4

BLOOD PLASMA HMB CONCENTRATIONS (mg/100 g of plasma)

| COMPOUND | Time after administration | 0 | 10 mins | 20 mins | 30 mins | 40 mins | 50 mins | 60 mins | 75 mins | 90 mins | 120 mins | 240 mins |
|---|---|---|---|---|---|---|---|---|---|---|---|---|
| HMB | COW 1 | 0.00 | 0.00 | 0.00 | 0.00 | 0.00 | 0.00 | 0.00 | 0.00 | 0.00 | 0.03 | 0.06 |
| HMB | COW 2 | 0.00 | 0.00 | 0.00 | 0.00 | 0.00 | 0.00 | 0.00 | 0.00 | 0.00 | 0.10 | 0.45 |
| HMB | COW 3 | 0.00 | 0.00 | 0.00 | 0.00 | 0.00 | 0.00 | 0.00 | 0.00 | 0.00 | 0.00 | 0.51 |
| HMB | COW 4 | 0.00 | 0.00 | 0.00 | 0.00 | 0.00 | 0.00 | 0.00 | 0.00 | 0.00 | 0.00 | 0.24 |
| Isopropyl ester of HMB | COW 1 | 0.00 | 4.02 | 4.19 | 3.64 | 3.40 | 3.11 | 2.71 | 2.35 | 2.23 | 1.78 | 0.58 |
| Isopropyl ester of HMB | COW 2 | 0.00 | 1.05 | 1.24 | 1.31 | 1.39 | 1.46 | 1.53 | 3.11 | 2.38 | 2.54 | 0.82 |
| Isopropyl ester of HMB | COW 3 | 0.00 | 0.28 | 0.93 | 1.45 | 1.96 | 1.99 | 2.37 | 2.94 | 3.49 | 3.11 | 1.09 |
| Isopropyl ester of HMB | COW 4 | 0.00 | 0.17 | 0.57 | 1.22 | 1.36 | 1.84 | 3.31 | 3.73 | 2.37 | 2.31 | 0.92 |

EXAMPLE 4

Milk Production

Example (a) Isopropyl Ester of the Hydroxy Analogue of Methionine and the Isopropyl Ester of Methionine The isopropyl ester of the hydroxy analogue of methionine was given to 16 cows over a period of 8 weeks. Each cow was given daily corn silage and a supplement to cover 100% of requirement and a 115% PDIE (protein digestible in the intestine) requirement. The daily supplement consisted of 4.3 kg of a high energy concentrate which consists of 19.8% barley, 21.1% wheat, 37.5% beet pulp, 2.3% animal fat, 1.1% salts, 0.6% calcium carbonate and 1.1% sodium bicarbonate; 2.2 kg of tanned soya cake, 1 kg of normal soya cake, 240 g of urea and 300 g of vitamin and mineral supplements.

The method according to the present invention was carried out by splitting the cows into three groups and giving the following supplement to the normal diet to provide 12.5 g of bioavailable methionine per animal per day.

Treatment 1: 1 kg of soya cake

Treatment 2: 1 kg of soya cake 20 g of polymer coated methionine (comparative example)

Treatment 3: 1 kg of soya cake supplemented with 3% isopropyl ester of HMBI containing 57% equivalent methionine Treatment 4: 1 kg of soya cake supplemented with 2.5% isopropyl ester of methionine containing 76% equivalent methionine.

The supplements were given to the cows according to the following schedule:

The results from the analyses of the milk produced are given below in Table 5

TABLE 5

RESULTS ON MILK PRODUCTION

| COMPOUND | Daily amount of milk (kg/cow) | Butter Content of Milk g/kg | Protein content of Milk g/kg |
|---|---|---|---|
| Control | 31.4 | 39.1 | 30.1 |
| isopropyl ester of methionine | 32.7 | 43.3 | 30.6 |
| isopropyl ester of HMB | 32.3 | 44.3 | 30.8 |
| COMPARATIVE: Polymer-protected methionine | 31.4 | 40.3 | 30.9 |

It can be seen from the results that the addition of the isopropyl esters of methionine and the isopropyl ester of the hydroxy analogue of methionine to the diet of the cow results in milk with higher fat content and higher protein content,

EXAMPLE 5

Liver and Fertility

The procedure of Example 4 was repeated and observations on the liver function and fertility of the cows were made. Substantial improvements were observed in the cows receiving the esters.

| | | PERIOD | | |
|---|---|---|---|---|
| Group* | D1 to D15 | D15 to D30 | D31 to D45 | D46 to D60 |
| 1 | Control without additive | isopropyl ester of HMB | isopropyl ester of methionine | Polymer-protected methionine |
| 2 | isopropyl ester of methionine | Control without additive | Polymer-protected methionine | isopropyl ester of HMB |
| 3 | isopropyl ester of HMB | Polymer-protected methionine | Control without additive | isopropyl ester of methionine |
| 4 | Polymer-protected methionine | isopropyl ester of methionine | isopropyl ester of HMB | Control without additive |

*4 cows per group

EXAMPLE 6

Milk Production

The procedure of Example 4 was repeated using rations containing other esters the choice of ester was made in confirmation with the results reported in examples 1 and 2 which show that the bioavailability of methionine in the blood of dairy cows is improved when using the esters of the present invention and rations containing these esters. Improved milk is also obtained.

We claim:

1. A method for supplying bioavailable methionine to a dairy cow, which comprises administering to the cow the isopropyl ester of methionine.

2. A method as claimed in claim 1, wherein the isopropyl ester of methionine is administered to the cow by feeding to the cow a feed containing the isopropyl ester of methionine.

3. A method of improving milk obtained from a dairy cow, which comprises supplying to the cow the isopropyl ester of methionine.

4. A method as claimed in claim 3, wherein the improvement in the milk comprises increased protein content in the milk.

5. A method as claimed in claim 3, wherein the improvement in the milk comprises increased fat content in the milk.

6. A method of improving the condition of a cow, which comprises supplying to the cow the isopropyl ester of methionine.

7. A method as claimed in claim 6, wherein the improvement in condition of the cow comprises improved fertility.

8. A method as claimed in claim 6, wherein the improvement in condition of the cow comprises improved liver function.

9. A method as claimed in claim 6, wherein the improvement in condition of the cow comprises an increase in energy.

* * * * *